United States Patent

Pscherer et al.

[11] Patent Number: 6,008,248
[45] Date of Patent: Dec. 28, 1999

[54] HYDROLYSIS-OPTIMIZED LIPID EMULSIONS AND USE THEREOF

[75] Inventors: German Pscherer; Marco Junginger, both of Melsungen; Jörg Nehne, Guxhagen, all of Germany; Yvon A. Carpentier, Brüssel, Belgium

[73] Assignee: B. Braun Melsungen AG, Melsungen, Germany

[21] Appl. No.: 09/043,166

[22] PCT Filed: Nov. 23, 1996

[86] PCT No.: PCT/EP96/05184

§ 371 Date: Mar. 12, 1998

§ 102(e) Date: Mar. 12, 1998

[87] PCT Pub. No.: WO97/19683

PCT Pub. Date: Jun. 5, 1997

[30] Foreign Application Priority Data

Nov. 28, 1995 [DE] Germany .......................... 195 44 310

[51] Int. Cl.[6] ........................................................ A61K 31/19
[52] U.S. Cl. ................................................. 514/560; 514/943
[58] Field of Search .................................. 514/546, 560, 514/937, 943

[56] References Cited

U.S. PATENT DOCUMENTS

| 5,034,414 | 7/1991 | Wakabayashi et al. | 514/549 |
|---|---|---|---|
| 5,034,415 | 7/1991 | Rubin | 514/560 |
| 5,089,268 | 2/1992 | Katz | 424/450 |
| 5,444,054 | 8/1995 | Garleb et al. | 514/54 |
| 5,470,839 | 11/1995 | Laughlin et al. | 514/53 |
| 5,574,065 | 11/1996 | Trimbo | 514/546 |
| 5,840,757 | 11/1998 | Dutot | 514/560 |
| 5,874,470 | 2/1999 | Nehne et al. | 514/560 |

FOREIGN PATENT DOCUMENTS

| 0298293 | 6/1988 | European Pat. Off. . |
|---|---|---|
| 0311091 | 5/1989 | European Pat. Off. . |
| 0687418 | 12/1995 | European Pat. Off. . |
| 2542613 | 9/1984 | France . |
| 3409793 | 9/1984 | Germany . |
| 3721137 | 1/1989 | Germany . |

OTHER PUBLICATIONS

Simoens et al. Manipulation of Tissue Fatty Acid Profile by Intravenous Lipids in Dogs. Clinical Nutrition, vol. 14, No. 3, pp. 177–185. (1995).

Sato et al., "Hydrolysis of Mixed Lipid Emulsions Containing Medium–Chain and Long–Chain Triacylglycerol with Lipoprotein Lipase in Plasma–like Medium," *Journal of Parenteral and Enteral Nutrition,* vol. 18, No. 2, Mar.–Apr. 1994, pp. 112–118.

Hallberg, D., "An Experimental, Methodological and Clinical Study in Dog and Man," Acta Physiol. Scand, vol. 65, Supp. 254 (1965), p. 2–23.

NEFAC Test Booklet, "In Vitro Enzymatic Colorimetric Method for the Quantitative Determination of Non–Esterified (or Free) Fatty Acids (NEFA or FFA) in Serum," Wako Chemicals GmbH, West Germany (1987).

*Primary Examiner*—Robert H. Harrison
*Attorney, Agent, or Firm*—Christie, Parker & Hale, LLP

[57] ABSTRACT

The present invention pertains to hydrolysis-optimized isotonic lipid emulsions comprising medium-chain triglycerides (MCT), vegetable oils and fish oil, as well as their use for parenteral nutritition.

25 Claims, No Drawings

HYDROLYSIS-OPTIMIZED LIPID EMULSIONS AND USE THEREOF

This application is a Rule 371 of PCT/EP96/05184, filed Nov. 23, 1996.

The present invention pertains to hydrolysis-optimized isotonic lipid emulsions (fat emulsions) for parenteral administration, in particular for parenteral nutrition, and their use in situations of exaggerated inflammatory response (e.g. post-surgery, post-trauma, sepsis, inflammatory or wasting diseases) or of increased risk of vascular thrombosis and severe cardiac arrytlmia where it is important to avoid inflicting an exogeneous triglyceride accumulation while making free fatty acids available to different tissues of the body as rapidly as possible.

Lipid emulsions for parenteral nutrition serve to supply the body with fats in an intravenously acceptable dosage form when normal (oral) nutrition is impossible, compromised or medically contraindicated or when it is necessary to promptly modify the fatty acid pattern of the cells. The lipid emulsions currently available are prepared from vegetable oils (e.g. safflower or soybean oils); in some cases they also contain medium-chain triglycerides (MCT) and/or oils of marine origin (fish oils).

Long-chain triglycerides of vegetable or marine origin serve as an energy source and, when containing polyunsaturated fatty acids, as suppliers of essential fatty acids. The classification of such polyunsaturated fatty acids into omega-6 or omega-3 series types is based on chemical structural features, more precisely, on the distance of the first unsaturated bond from the methyl end (omega end) of the fatty acid molecule.

The vegetable oils, e.g. of soybean and safflower, are characterized by a high content of polyunsaturated fatty acids of the omega-6 series (predominantly linoleic acid, 18:2 n-6) whereas their content of omega-3 fatty acids (almost exclusively in the form of α-linolenic acid, 18:3 n-3) is low.

Fish oils obtained from cold-water fish are characterized by a high content of polyunsaturated fatty acids of the omega-3 series (predominantly eicosapentaenoic acid, EPA, 20:5 n-3, and docosahexenoic acid, DHA, 22:6 n-3) whereas their content of omega-6 fatty acids is low.

The medium-chain triglycerides administered with the lipid emulsions serve mainly as a source of energy. Medium-chain triglycerides do not contain any unsaturated fatty acids and hence contain neither omega-6 nor omega-3 essential fatty acids.

Numerous clinical observations underline the principal suitability of lipid emulsions for parenteral nutrition and for substituting essential fatty acids in severe diseases and the metabolic conditions involved.

The human body is itself incapable of producing the vital, polyunsaturated long-chain fatty acids of the omega-6 or omega-3 series; i.e. they have to be administered orally, enterally or parenterally. The body is only able to synthesize longer-chain unsaturated fatty acids from shorter-chain ones; formation of omega-6 fatty acids from precursors of the omega-3 series or vice versa is impossible, however.

Correspondingly, there is a need for lipid emulsions for parenteral administration which contain medium-chain triglycerides as well as triglycerides of omega-6 and omega-3 fatty acids as lipid components.

EP-A-0 311 091 describes isotonic lipid emulsions for parenteral nutrition comprising, in addition to conventional additives and auxiliary agents, omega-3 fatty acids, omega-3 fatty acids in the form of their esters or as components of fish oils, medium-chain triglycerides, as well as optionally at least one vegetable oil providing omega-6 fatty acids in a proportion of up to 30%, based on the lipid content of the emulsion.

DE-OS-37 21 137 describes lipid emulsions for parenteral nutrition comprising eicosapentaenoic acid triglyceride and/or docosahexaenoic acid triglyceride, or fish oils containing such triglycerides, as well as vegetable oils containing omega-6 fatty acids, and medium-chain triglycerides.

DE-OS-34 09 793 describes a lipid emulsion for transfusion comprising a fatty acid containing from 20 to 22 carbon atoms, esters thereof, or a mixture of 2 or more of such fatty acids or esters, as well as a vegetable oil, an emulsifier, and water. Said fatty acids are fatty acids from esters of marine origin (fish oils), in particular omega-3 fatty acids. Said vegetable oils are purified soybean and/or safflower oils.

In order that the exogeneous free fatty acids are made available to the body, they must either be released hydrolytically from the infused triglycerides by means of the enzyme lipoprotein lipase (LPL) or he taken up together with emulsion particles or their remnants directly into the cells. This initial step of lipidhydrolysis has long been considered the rate-determining step of lipid metabolism. This limitation arises from the relatively limited activity of lipoprotein lipase in cleaving triglycerides Thus, the maximum metabolizing rate for vegetable oil emulsions is about 3.8 g of lipid/kg body weight per day (Hallberg et al., Acta Physiol. Scand., Vol. 65, Suppl. 254 (1965), p. 2–23).

During triglyceride infusion, it is desirable, to achieve triglyceride serum concentrations which are as low as possible, e.g. corresponding to a low load of the reticuloendothelial system (RES) by exogenous lipid.

Typically, post-operative and post-traumatic conditions as well as severe septic episodes are characterized by a substantial stimulation of the immune system. The immune response involves the release of cytokines (e.g. tumor necrosis factor and inter-leukins) which, at high levels, may cause severe tissue damage. In addition, high cytokine concentrations also impair hydrolysis of circulating triglycerides by LPL.

In such clinical conditions, it is of particular importance to use exogenous triglycerides which are rapidly hydrolyzed and eliminated and which contain fatty acids (e.g. omega-3 fatty acids) capable of reducing cytokine production as well as cytokine toxicity on tissues.

Fatty acids as an energy substrate (for oxidative purposes) and for incorporation in membranes (for structural purposes) and as precursors of eicosanoids should also be made available to the body as quickly as possible.

Triglycerides typical of fish oils are hydrolyzed much more slowly than triglycerides from vegetable oils (e.g. soybean oil) which are themselves hydrolyzed more slowly than medium-chain triglycerides. Addition of a fish oil emulsion to a long-chain triglyceride emulsion can even inhibit hydrolysis of long-chain triglycerides (e.g. from soybean oil) by LPL.

Therefore, it is an object of the invention to provide a lipid emulsion for parenteral nutrition capable of being parenterally administered which has been optimized with respect to hydrolysis and elimination, which means that the triglycerides supplied with said lipid emulsion are hydrolyzed in the body extra- or intracellularly, i.e. cleaved to free fatty acids and glycerol, as quickly as possible without concomitant excessive increase of the serum level of free fatty acids. This implies that more lipids can be administered to the body parenterally within the same period of time without an increase of lipid concentration or concentration of hydrolysis products.

This object has been achieved by a hydrolysis-optimized isotonic aqueous lipid emulsion for parenteral administration comprising, based on the total lipid content of the lipid emulsion:

from 30% to 60% by weight of medium-chain triglycerides;

from 35% to 65% by weight of at least one vegetable oil comprising triglycerides which supply omega-6 fatty acids;

from 5% to 20% by weight of at least one fish oil comprising triglycerides which supply omega-3 fatty acids; and conventional auxiliary agents and/or additives.

Surprisingly, it has been found that the object of the invention may be achieved by combining in the same emulsion particle medium-chain triglycerides, vegetable oils rich in omega-6 fatty acids, and fish oils containing omega-3 fatty acids in the quantitative proportion mentioned above. In particular, it has been found that the MCT/vegetable oil/fish oil mixtures of the invention are more quickly hydrolyzed than known MCT/vegetable oil mixtures and MCT/vegetable oil/fish oil mixtures of the prior art. Thus, triglyceride load of the body by exogeneous triglycerides is avoided. Medium-chain fatty acids and long-chain essential fatty acids become quickly available to the body. This involves no significant increase of the serum concentration of free fatty acids despite the fact that more lipids are supplied to the body per unit of time. Further, rapid incorporation of omega-3 fatty acids in platelet and leucocyte membrane phospholipids can be observed.

The lipid emulsions according to the invention include emulsified mixtures of oils (lipids) rather than mixtures of the emulsions.

According to the invention, those medium-chain triglycerides are used which have chain lengths of fatty acid ranging from $C_6$ to $C_{14}$ and which are comprised of at least 90% by weight of triglycerides of caprylic acid ($C_8$) and capric acid ($C_{10}$). The fraction of medium-chain triglycerides, based on the total lipid content of the lipid emulsion, is preferably from 45% to 55%, more preferably from 48% to 52%, by weight.

The lipid emulsions according to the invention further contain at least one vegetable oil containing triglycerides made predominantly of omega-6 fatty acids.

Preferred vegetable oils are safflower oil and/or soybean oil, the content of such vegetable oils in the lipid emulsion preferably being from 35% to 45%, more preferably from 38% to 42%, by weight, based on the lipid content of the lipid emulsion. The vegetable oils contain triglycerides of fatty acids having chain lengths of $C_{16}$ to $C_{20}$ and predominantly contain triglycerides of omega-6 fatty acids.

Fish oils are known to contain eicosapentaenoic acid (EPA, 20:5 n-3) and docosahexaenoic acid (DHA, 22:6 n-3) incorporated in triglycerides which, being so-called highly unsaturated omega-3 fatty acids, are essential building blocks which have to be supplied to the body and which are biologically important, for example, as precursors of eicosanoids and as structural elements of membrane lipids. These acids are further attributed antithrombotic and lipid-lowering actions. Since their isolation from natural products and their chemical synthesis is expensive, fish oils, being relatively inexpensive, are the suppliers of choice for such essential fatty acids. As used in the invention, the term "fish oils" is intended to comprise natural fish oils, processed fish oils, or highly purified fish oil concentrates. According to the invention, processed fish oils may also be used, such as described e.g. in EP-A-0 298 293 which is incorporated herein by reference.

Suitable exemplary fish oils are oils which are obtained from cold water fish on a technically significant scale or oils which are synthetically obtainable by esterification of omega-3-fatty acids (obtained from fish oil of cold water fish, preferably salmon, sardine, mackerel, herring, anchovy, smelt and swordfish, by hydrolysis of the triglycerides and subsequent purification and concentration of the resultant omega-3-fatty acids) with glycerol. Fish oils generally contain triglycerides of fatty acids having chain lengths of from 12 to 22 carbon atoms. Particularly preferred are highly purified fish oil concentrates which are obtained, for instance, from sardine, salmon, herring and/or mackerel oils. They have an eicosapentaenoic acid content of from 20 to 40%, preferably at least 25%, based on the fatty acid methyl esters of the fish oil concentrate as determined by gas chromatography (percent by area). Furthermore, they have a docosahexaenoic acid content of from 10 to 20%, preferably at least 12%, based on the fatty acid methyl esters of the fish oil concentrate as determined by gas chromatography (percent by area). In case of the fish oils which are synthetically obtainable by the re-esterification of the omega-3-fatty acids the total concentration of eicosapentaenoic+docosahexaenoic acid can be at least 45% on basis of the triglycerides.

It is particularly preferred to use a fish oil rich in EPA when inflammatory processes are to be influenced. Fish oil rich in DHA is particularly preferred in pediatric patients in the case of omega-3 fatty acid deficiency to influence growth and maturation of the central nervous system.

Preferably, the content of fish oil, based on the total lipid content of the lipid emulsion, is from 10% to 20%, more preferably from 10% to 14%, by weight.

The total lipid content of the lipid emulsion is from 5% to 30%, preferably from 10% to 25%, by weight, based on the aqueous lipid emulsion.

In addition to distilled water, the isotonic lipid emulsion contains the usual auxiliary agents and/or additives, such as emulsifiers, emulsifying aids (co-emulsifiers), stabilizers. antioxidants, and isotonizing additives.

As emulsifiers, physiologically acceptable emulsifiers are used, such as phospholipids of animal or vegetable origin. Particularly preferred are purified lecithins, especially soybean lecithin, egg lecithin, or fractions thereof, or the corresponding phosphatides. The emulsifier content is from 0.6% to 1.5%, preferably 1.2%, by weight, based on the total emulsion.

Further, alkali metal salts of long-chain, $C_{16}$ to $C_{20}$, fatty acids may be used as emulsifying aids (co-emulsifiers). Especially preferred are their sodium salts. The co-emulsifiers are employed in concentrations of from 0.005% to 0.1%, preferably 0.02% to 0.04%, by weight, based on the total emulsion. Further, cholesterol or a cholesterol ester alone or in combination with other co-emulsifiers may be employed in a concentration of from 0.005% to 0.1%, preferably from 0.02% to 0.04%, by weight.

The lipid emulsion according to the invention may contain vitamin E, in particular α-tocopherol, and/or ascorbyl palmitate as antioxidants and thus for protection from peroxide formation in amounts of from 10 to 1000 mg, preferably 25 to 200 mg, based on 100 g of lipid.

For stabilization and isotonization, the emulsion according to the invention may contain from 2% to 5% by weight of a stabilizing or isotonizing additive, for example, a polyhydric alcohol. In this connection, glycerol, sorbitol, xylitol or glucose are preferred, glycerol being particularly preferred.

The lipid emulsions according to the invention are invariably oil-in-water (o/w) emulsions in which the outer, continuous phase consists of distilled water purified for parenteral purposes Such o/w emulsion is obtained by mixing MCT, vegetable oil and fish oil and subsequent emulsification. After sterilization, the lipid emulsion has a pH of from 6.0 to 9.0, preferably from 6.5 to 8.5.

The isotonic lipid emulsions according to the invention can be prepared by known procedures with inertization. The usual approach is first to mix the lipids, emulsifier and other auxiliary agents and additives and then to fill up with water with dispersing. The water may optionally contain additional water-soluble components (e.g. glycerol). The emulsion thus obtained still contains lipid particles having a diameter of about 10 μm. The average droplet size of the emulsion must then further be reduced by additional homogenization, e.g. using a high-pressure homogenizer. For parenteral application, medium lipid droplet sizes of less than 1.0 μm, in particular less than 0.5 μm, are preferred.

The lipid emulsions according to the invention are used for parenteral administration, in particular parenteral nutrition, of patients with exaggerated inflammatory responses or increased risk of vascular thrombosis or severe cardiac arrythmia. In particular, the lipid emulsions according to the invention can be used with patients in post-operative and post-traumatic conditions or inflammatory diseases; further, e.g., in severe or persistent post-aggression metabolism following operations, such as abdominal operations or organ transplantations, and multiple trauma, inflammatory diseases, burns, infections, impending or manifest sepsis, impaired respiratory function, conditions of excessive production of cytokines, wasting diseases, and increased risk of severe cardiac arrythmia (e.g. ventricular fibrillation) or vascular thrombosis. The lipid emulsion according to the invention can also be used for parenteral nutrition following shock conditions for improving microperfusion and metabolic performance of organs poorly supplied with blood in terms of metabolic reanimation.

The invention will be illustrated by the following examples.

PREPARATIVE EXAMPLES

Table 1 shows the fatty acid composition (approx. %) of various oils used in the lipid emulsions of the following examples:

TABLE 1

| Fatty acid | MCT oil[1] | Soybean oil[2] | Safflower oil[3] | Fish oil[4] |
|---|---|---|---|---|
| 6:0 | <2 | — | — | — |
| 8:0 | 64 | — | — | — |
| 10:0 | 34 | — | — | — |
| 12:0 | <3 | — | — | <1 |
| 14:0 | <1 | — | — | 5 |
| 16:0 | — | 11 | 7 | 10 |
| 16:1 | — | — | — | 7 |

TABLE 1-continued

| Fatty acid | MCT oil[1] | Soybean oil[2] | Safflower oil[3] | Fish oil[4] |
|---|---|---|---|---|
| 16:2 | — | — | — | 1 |
| 16:3 | — | — | — | 1 |
| 16:4 | — | — | — | 3 |
| 18:0 | — | 4 | 3 | 1 |
| 18:1 | — | 22 | 14 | 10 |
| 18:2 n-6 | — | 55 | 75 | 2 |
| 18:3 n-3 | — | 8 | <1 | 1 |
| 18:4 n-3 | — | — | — | 4 |
| 20:0 | — | <1 | <1 | — |
| 20:1 | — | <1 | <1 | 2 |
| 20:4 n-6 | — | — | — | 2 |
| 20:5 n-3 | — | — | — | 28 |
| 22:1 | — | — | — | 1 |
| 22:4 | — | — | — | <1 |
| 22:5 | — | — | — | 3 |
| 22:6 n-3 | — | — | — | 13 |
| Σ n-6 | — | 55 | 75 | 4 |
| Σ n-3 | — | 8 | <1 | 46 |
| n-6:n-3 | — | 7:1 | ≧75:1 | 1:12 |

[1] medium chain triglycerides, e.g. Captex 355, commercial product of Karlshamns.
[2] soybean oil, e.g. Sojaol, commercial product of Croda.
[3] safflower oil, e.g. Saflorol, commercial product of Gustav Heess.
[4] highly purified fish oil, e.g. Sanomega S2BGA, commercial product of Nippon Oil and Fats.

Mixture I containing MCT, vegetable oil, fish oil, emulsifier (fractionated phospholipids from chicken egg yolk) is dispersed by means of Ultra-Turrax and filled up with aqueous component II with stirring. The pH value is adjusted to pH 8.0 to 9.0 using an aqueous sodium hydroxide solution and/or sodium oleate. Subsequent homogenization is performed in a high-pressure homogenizer at 400 kg/cm². After dispensing in glass bottles of appropriate grade, heat sterilization is performed by known methods.

TABLE 2

| | Preparative Example | 1 (comparative example 1*) | 2 | 3 | 4 | 5 (comparative example 2**) |
|---|---|---|---|---|---|---|
| I. | medium-chain triglycerides from partial synthesis | 1000 g | 500 g | 1000 g | 1000 g | 1000 g |
| | purified safflower oil | — | — | 800 g | — | — |
| | purified soybean oil | 1000 g | 400 g | — | 800 g | 600 g |
| | highly purified fish oil | — | 100 g | 200 g | 200 g | 400 g |
| | cholesterol acetate | — | — | 2 g | — | — |
| | purified phospholipids from: | 120 g egg | 90 g egg | 120 g egg | 120 g egg | 120 g egg |
| | α-tocopherol | 2000 mg | 1000 mg | 2000 mg | 2000 mg | 2000 mg |
| | ascorbyl palmitate | 1500 mg | — | 1000 mg | 1500 mg | 1500 mg |
| | sodium oleate | 3,0 g | 2,5 g | — | 3,0 g | 3,0 g |
| II. | glycerol | 250 g | 250 g | 250 g | 250 g | 250 g |
| | NaOH | — | — | to pH 8.0–9.0 | — | — |
| | water for injections | ad 10 l | ad 10 l | ad 10 l | ad 10 l | ad 10 l |

*MCT/vegetable oil (50:50)
**MCT/vegetable oil/fish oil (50:30:20) according to EP-A-O 311 091

A sterile and pyrogen-free, stable emulsion resulted containing lipid droplets having an average size of less than 0.5 μm with a shelf-life at room temperature of at least 18 months.

EXAMPLE 1

(in vivo)
1. Determination of Triglyceride Hydrolysis

Eight male subjects (age (av. ±st.d.) 23±3 years) were infused with a lipid emulsion of MCT/vegetable oil (50:50) over 5 h each on 4 successive days (treatment A, table 3; preparative example 1 in table 2). After an interval of four weeks, a lipid emulsion of MCT/vegetable oil/fish oil (50:40:10) was infused under the same conditions (treatment B, table 4; preparative example 4 in table 2). After another interval of at least eight weeks, a lipid emulsion of MCT/vegetable oil/fish oil (50:30:20) was infused under the same conditions (treatment C, table 5; preparative example 5 in table 2). Triglyceride hydrolysis in the serum (measured as the average infusion rate in mg of lipids/kg body weight/h under triglyceride clamp conditions at a serum concentration of 3.0 mmol/l from 3rd to 5th hours of infusion, 9 measurements per subject and per day; analysis of variance) was determined as follows:

TABLE 3

Treatment A (Comparative Example 1)
Average infusion rate (3rd to 5th hour) with an MCT/vegetable oil (50:50) emulsion [mg of lipids/kg body weight/h]

| Subject | Day 1 | Day 2 | Day 3 |
| --- | --- | --- | --- |
| 1. | 171 | 155 | 180 |
| 2. | 98 | 103 | 101 |
| 3. | 142 | 161 | 122 |
| 4. | 180 | 175 | 166 |
| 5. | 182 | 223 | 243 |
| 6. | 203 | 259 | 269 |
| 7. | 129 | 129 | 143 |
| 8. | 188 | 221 | 170 |
| average ± st.d. | 162 ± 35 | 178 ± 53 | 174 ± 57 |

TABLE 4

Treatment B (according to the invention)
Average infusion rate (3rd to 5th hour) with an MCT/vegetable oil/fish oil (50:40:10) emulsion [mg of lipids/kg bodyweight/h]

| Subject | Day 1 | Day 2 | Day 3 |
| --- | --- | --- | --- |
| 1. | 224 | 236 | 203 |
| 2. | 201 | 134 | 163 |
| 3. | 186 | 199 | 182 |
| 4. | 190 | 201 | 179 |
| 5. | 255 | 278 | 273 |
| 6. | 259 | 272 | 271 |
| 7. | 147 | 154 | 142 |
| 8. | 176 | 182 | 181 |
| average ± st.d. | 205 ± 39 | 207 ± 52 | 199 ± 48 |

TABLE 5

Treatment C (Comparative Example 2)
Average infusion rate (3rd to 5th hour) with an MCT/vegetable oil/fish oil (50:30:20) emulsion [mg of lipids/kg body weight/h]

| Subject | Day 1 | Day 2 | Day 3 |
| --- | --- | --- | --- |
| 1. | 202 | 192 | 186 |
| 2. | 133 | 122 | 120 |
| 3. | 147 | 148 | 174 |
| 4. | 228 | 211 | 204 |
| 5. | 233 | 241 | 231 |
| 6. | 168 | 250 | 259 |
| 7. | 147 | 189 | 161 |
| 8. | 174 | 177 | 188 |
| average ± st.d. | 179 ± 36 | 191 ± 41 | 190 ± 40 |

Triglyceride hydrolysis under treatment B according to the invention was significantly higher than that under treatments A ($p<0.0001$) and C ($p<0.05$) for all days of treatment. Thus, the average infusion rate over three days was 4.9 g of triglycerides/kg body weight/day for the lipid emulsion of MCT/vegetable oil/fish oil (50:40:10), and 4.1 and 4.5 g of triglycerides/kg body weight/day, respectively, for the lipid emulsions of MCT/vegetable oil (50:50) and MCT/vegetable oil/fish oil (50:30:20). The lipid emulsions composed according to preparative examples 2 and 3 give similar results. The result of a more rapid hydrolyzation of the lipid emulsions according to the invention to give free fatty acids as compared to the concentional lipid emulsions of the prior art can also be confirmed by in vitro studies (cf. example 2).

2. Determination of the Level of Free Fatty Acids in the Serum

The level of free fatty acids in the serum of the subjects was determined on the days of treatment before (0 h) and immediately following (5 h) administration of the lipid emulsion. A suitable test for this purpose is, for instance, NEFAC test (an in vitro enzymatic colorimetric method) of Wako Chemicals GmbH, Germany.

It has been found that upon administration of the lipid emulsion of MCT/vegetable oil/fish oil (50:40:10) according to the invention the serum concentrations of free fatty acids are not increased to markedly higher values as compared to administration of a commercial lipid emulsion of MCT/vegetable oil (50:50) and another lipid emulsion of MCT/vegetable oil/fish oil (50:30:20) although more lipids have been supplied to the body per unit of time. The experimental results are given hereinafter in tables 6 and 7:

TABLE 7

Treatment B (according to the invention)
Free Fatty Acids in the Serum [$\mu$mol/l],
MCT/vegetable oil/fish oil (50:40:10)

| Subject | after | Day 1 | Day 2 | Day 3 |
| --- | --- | --- | --- | --- |
| 1. | 0 h | 18 | 0 | 28 |
|  | 5 h | 1321 | 1421 | 1102 |
| 2. | 0 h | 298 | 254 | 431 |
|  | 5 h | 1252 | 1101 | 1038 |
| 3. | 0 h | 7 | 14 | 26 |
|  | 5 h | 1363 | 1286 | 1239 |
| 4. | 0 h | 25 | 8 | 7 |
|  | 5 h | 1179 | 1197 | 1095 |
| 5. | 0 h | 0 | 11 | 30 |
|  | 5 h | 1165 | 1502 | 1381 |
| 6. | 0 h | 4 | 0 | 19 |
|  | 5 h | 1556 | 1295 | 1417 |
| 7. | 0 h | 70 | 88 | 75 |
|  | 5 h | 1053 | 983 | 963 |
| 8. | 0 h | 0 | 12 | 0 |
|  | 5 h | 1421 | 941 | 1012 |
| Average ± st.d. | 0 h | 53 ± 95 | 48 ± 82 | 77 ± 135 |
|  | 5 h | 1289 ± 150 | 1216 ± 187 | 1156 ± 160 |

TABLE 6

Treatment A (Comparative Example 1)
Free Fatty Acids in the Serum [$\mu$gmol/l], MCT/vegetable oil (50:50)

| Subject | after | Day 1 | Day 2 | Day 3 |
| --- | --- | --- | --- | --- |
| 1. | 0 h | 0 | 22 | 39 |
|  | 5 h | 921 | 921 | 1068 |
| 2. | 0 h | 399 | 202 | 143 |
|  | 5 h | 996 | 742 | 762 |
| 3. | 0 h | 57 | 48 | 48 |
|  | 5 h | 1554 | 144 | 1408 |
| 4. | 0 h | 52 | 71 | 44 |
|  | 5 h | 1212 | 1173 | 979 |
| 5. | 0 h | 20 | 23 | 10 |
|  | 5 h | 903 | 1272 | 1405 |
| 6. | 0 h | 28 | 41 | 82 |
|  | 5 h | 1082 | 1271 | 1449 |
| 7. | 0 h | 97 | 90 | 122 |
|  | 5 h | 1068 | 949 | 1169 |
| 8. | 0 h | 27 | 47 | 34 |
|  | 5 h | 1219 | 1236 | 1140 |

TABLE 6-continued

Treatment A (Comparative Example 1)
Free Fatty Acids in the Serum [μgmol/l], MCT/vegetable oil (50:50)

| Subject | after | Day 1 | Day 2 | Day 3 |
|---|---|---|---|---|
| Average ± st.d. | 0 h | 85 ± 122 | 68 ± 55 | 65 ± 43 |
|  | 5 h | 1119 ± 198 | 1126 ± 218 | 1173 ± 225 |

TABLE 8

Treatment C (Comparative Example 2)
Free Fatty Acids in the Serum [μmol/l], MCT/vegetable oil/fish oil (50:30/20)

| Subject | after | Day 1 | Day 2 | Day 3 |
|---|---|---|---|---|
| 1. | 0h | 13 | 12 | 0 |
|  | 5h | 1051 | 828 | 863 |
| 2. | 0h | 271 | 67 | 82 |
|  | 5h | 900 | 816 | 899 |
| 3. | 0h | 0 | 20 | 1 |
|  | 5h | 1010 | 941 | 1006 |
| 4. | 0h | 32 | 136 | 128 |
|  | 5h | 1175 | 1269 | 1229 |
| 5. | 0h | 0 | 10 | 0 |
|  | 5h | 1139 | 1159 | 1024 |
| 6. | 0h | 15 | 34 | 21 |
|  | 5h | 887 | 1252 | 1239 |
| 7. | 0h | 180 | 283 | 177 |
|  | 5h | 1340 | 1335 | 1135 |
| 8. | 0h | 0 | 0 | 0 |
|  | 5h | 873 | 811 | 852 |
| Average ± st.d. | 0h | 64 ± 97 | 70 ± 90 | 51 ± 65 |
|  | 5h | 1047 ± 154 | 1051 ± 211 | 1031 ± 146 |

3. Determination of Eicosapentaenoic Acid (EPA, 20:5 n-3) Incorporation in Membrane Phospholipids of Platelets (Thrombocytes) and Leucocytes The determination of the proportion of eicosapentaenoic acid in the membrane phospholipids of the thrombocytes and leucocytes of the eight subjects was performed by gas chromatography via the fatty acid methyl esters (percent by area method).

TABLE 9

Treatment B (according to the invention)
Eicosapentaenoic in thrombocytes and leucocytes,
MCT/vegetable oil/fish oil (50:40:10)

|  | Day 1 (0 h) | Day 2 (0 h) | Day 3 (0 h) |
|---|---|---|---|
| EPA in thrombocytes Average ± st.d. (% by area) | 0.2 ± 0.1 | 0.7 ± 0.1 | 1.2 ± 0.1 |
| EPA in leucocytes Average ± st.d. (% by area) | 0.4 ± 0.1 | 0.7 ± 0.3 | 1.0 ± 0.3 |

TABLE 10

Treatment C (Comparative Example 2)
Eicosapentaenoic in thrombocytes and leucocytes,
MCT/vegetable oil/fish oil (50:30/20)

|  | Day 1 (0 h) | Day 2 (0 h) | Day 3 (0 h) |
|---|---|---|---|
| EPA in thrombocytes Average ± st.d. (% by area) | 0.4 ± 0.1 | 1.0 ± 0.1 | 1.7 ± 0.1 |
| EPA in leucocytes Average ± st.d. (% by area) | 0.4 ± 0.1 | 0.9 ± 0.1 | 1.4 ± 0.1 |

A comparison of the results of table 9 with those of table 10 shows that in treatment C, for example, an EPA contents of 0.9% by area was found in leucocytes on day 2. From the fish oil content in treatment B according to the invention being only half as high, an EPA content of 0.45% by area would be expected. Surprisingly, however, a significantly higher value was found, namely 0.7% by area. A similar result is obtained for day 3 as well as for thrombocytes on days 2 and 3.

EXAMPLE 2

(in vitro)
Apoprotein Uptake into the Emulsion Particles

Of great interest is the significantly lower enrichment (t-test, two-sided) of apoprotein C-I ($p<0.0001$) and apoprotein C-III ($p<0.0001$), which are both apoproteins that inhibit both, triglyceride hydrolysis and direct uptake of the emulsion particles into the target tissue (such as the liver), in the emulsion particles having a composition according to the invention (preparation example 4) will presumably result in a more thorough intravascular scavenging of lipids than with the other lipid emulsion examined (preparation example 5).

TABLE 11

Uptake of Apoproteins C-I and C-III in Emulsion Particles,
(incubation: 3 h), MCT/vegetable oil/fish oil (50.40:10) vs.
MCT/vegetable oil/fish oil (50:30:20)

|  | MCT/vegetable oil/fish oil (50:40:10) (Preparative Example 4) | MCT/vegetable oil/fish oil (50:30:20) (Preparative Example 5) |
|---|---|---|
| Apo C-I Uptake [μg] Average ± st.d. | 5.1 ± 0.51 (n = 4) | 23.4 ± 1.43 (n = 4) |
| Apo C-III Uptake [μg] Average ± st.d. | 30.1 ± 2.67 (n = 4) | 54.7 ± 4.00 (n = 4) |

Lipid emulsions for parenteral administration will interact with endogeneous lipoproteins. During the infusion, the exogeneously supplied emulsion partly fuses with endogeneous LDL (low density lipoprotein; d<1.006 g/ml), a lipoprotein with a high content of apoprotein B (apo B). Thus, the apo B enrichment in the fused emulsion particles is indicative of the extent of fusion of exogeneously supplied emulsion with endogeneous LDL which has a relatively long plasma half life. Therefore, a high content of apo B in the fused emulsion particles must be considered indicative of prolonged residence time of the infused lipids. Conversely, a low apo B content means a short plasma half life, corresponding to a reduced residence time in the plasma.

Two lipid emulsions according to preparative examples 4 and 5 were incubated with human LDL in lipoprotein-poor plasma at 37° C. for 4 hours, followed by a determination of the content of apoprotein B in the emulsion fraction.

TABLE 12

Apoprotein B Content in the Emulsion Particles,
MCT/vegetable oil/fish oil (50:40:10) vs.
MCT/vegetable oil/fish oil (50:30:20)

|  | MCT/vegetable oil/fish oil (50:40:10) (Preparative Example 4) | MCT/vegetable oil/fish oil (50:30:20) (Preparative Example 5) |
|---|---|---|
| Apo B Content [mg/dl] Average ± st.d. | 0.05 ± 0.05 (n = 6) | 0.27 ± 0.21 (n = 7) |

The emulsion particles having a composition according to the invention show an apo B enrichment which is more than five times lower than that of the other lipid emulsion examined, corresponding to a higher hydrolysis rate. The difference is significant (t-test, two-sided; p<0.05).

We claim:

1. An isotonic lipid emulsion for parenteral administration comprising lipid droplets, wherein each such droplet comprises medium-chain triglycerides, at least one vegetable oil comprising triglycerides which supply omega-6-fatty acids, and at least one fish oil comprising triglycerides which supply omega-3-fatty acids wherein said lipid emulsion comprises, based on the total lipid content of the emulsion:

from 30% to 60% by weight of the medium-chain triglycerides;

from 35% to 65% by weight of the vegetable oil(s); and from 5% to 20% by weight of the fish oil(s).

2. The lipid emulsion according to claim 1, wherein said medium-chain triglycerides comprise at least 90% triglycerides of caprylic acid ($C_8$) and capric acid ($C_{10}$).

3. The lipid emulsion according to claim 1, wherein said vegetable oil is selected from the group consisting of safflower oil and soybean oil.

4. The lipid emulsion according to claim 1, wherein said fish oil is selected from the group consisting of sardine, salmon, herring, mackerel and other cold water fish oils and fish oils synthetically obtainable by re-esterification of glycerol with omega-3-fatty acids obtained by hydrolysis of cold water fish oil.

5. The lipid emulsion according to claim 1, wherein said fish oil contains at least 25% of eicosapentaenoic acid in said triglycerides, based on the fatty acid methyl esters of the fish oil concentrate.

6. The lipid emulsion according to claim 1, wherein said fish oil contains at least 12% of docosahexaenoic acid in said triglycerides, based on the fatty acid methyl esters of the fish oil concentrate.

7. The lipid emulsion according to claim 1, wherein the total lipid content is from 5% to 30% by weight, based on the weight of the emulsion.

8. A method for treating exaggerated inflammatory reactions, increased risk of vascular thrombosis or severe cardiac arrythmia by parenteral administration of the emulsion of claim 1 to a patient having an exaggerated inflammatory reaction, or an increased risk of vascular thrombosis, or severe cardiac arrythmia.

9. The lipid emulsion according to claim 1, wherein the average size of the said lipid droplets is less than 1.0 μm.

10. The lipid emulsion according to claim 2, wherein said vegetable oil is selected from the group consisting of safflower oil and soybean oil.

11. The lipid emulsion according to claim 2, wherein said fish oil is selected from the group consisting of sardine, salmon, herring, mackerel and other cold water fish oils and fish oils synthetically obtainable by re-esterification of glycerol with omega-3-fatty acids obtained by hydrolysis of cold water fish oil.

12. The lipid emulsion according to claim 3, wherein said fish oil is selected from the group consisting of sardine, salmon, herring, mackerel and other cold water fish oils and fish oils synthetically obtainable by re-esterification of glycerol with omega-3-fatty acids obtained by hydrolysis of cold water fish oil.

13. The lipid emulsion according to claim 2, wherein said fish oil contains at least 25% of eicosapentaenoic acid in said triglycerides, based on the fatty acid methyl esters of the fish oil concentrate.

14. The lipid emulsion according to claim 3, wherein said fish oil contains at least 25% of eicosapentaenoic acid in said triglycerides, based on the fatty acid methyl esters of the fish oil concentrate.

15. The lipid emulsion according to claim 4, wherein said fish oil contains at least 25% of eicosapentaenoic acid in said triglycerides, based on the fatty acid methyl esters of the fish oil concentrate.

16. The lipid emulsion according to claim 2, wherein said fish oil contains at least 12% of docosahexaenoic acid in said triglycerides, based on the fatty acid methyl esters of the fish oil concentrate.

17. The lipid emulsion according to claim 3, wherein said fish oil contains at least 12% of docosahexaenoic acid in said triglycerides, based on the fatty acid methyl esters of the fish oil concentrate.

18. The lipid emulsion according to claim 4, wherein said fish oil contains at least 12% of docosahexaenoic acid in said triglycerides, based on the fatty acid methyl esters of the fish oil concentrate.

19. The lipid emulsion according to claim 5, wherein said fish oil contains at least 12% of docosahexaenoic acid in said triglycerides, based on the fatty acid methyl esters of the fish oil concentrate.

20. The lipid emulsion according to claim 2, wherein the total lipid content is from 5% to 30% by weight, based on the weight of the emulsion.

21. The lipid emulsion according to claim 3, wherein the total lipid content is from 5% to 30% by weight, based on the weight of the emulsion.

22. The lipid emulsion according to claim 4, wherein the total lipid content is from 5% to 30% by weight, based on the weight of the emulsion.

23. The lipid emulsion according to claim 5, wherein the total lipid content is from 5% to 30% by weight, based on the weight of the emulsion.

24. The lipid emulsion according to claim 6, wherein the total lipid content is from 5% to 30% by weight, based on the weight of the emulsion.

25. A method for treating exaggerated inflammatory reactions, increased risk of vascular thrombosis, or severe cardiac arrythmia by parenteral administration of an emulsion provided in accordance with claim 2 to a patient having an exaggerated inflammatory reaction, or an increased risk of vascular thrombosis, or severe cardiac arrythmia.

* * * * *